(12) United States Patent
Jany (10) Patent No.: US 6,207,177 B1
(45) Date of Patent: Mar. 27, 2001

(54) MONOSODIUM CYANURIC ACID SLURRY

(75) Inventor: John R. Jany, Chesterfield, MO (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 08/921,828

(22) Filed: Sep. 2, 1997

(51) Int. Cl.$^7$ ..................................................... A01N 25/04
(52) U.S. Cl. ......................... 424/405; 504/133; 504/212; 514/241
(58) Field of Search .................................. 504/133, 212; 424/405, 241; 514/944

(56) References Cited

U.S. PATENT DOCUMENTS

| | | |
|---|---|---|
| 4,233,444 | 11/1980 | Doonan . |
| 4,432,959 | 2/1984 | Shimamura . |
| 5,066,408 | 11/1991 | Powell . |

*Primary Examiner*—Neil S. Levy
(74) *Attorney, Agent, or Firm*—Richard D. Fuerle; Anne E. Brookes (57) ABSTRACT

Disclosed is a stable gel-like slurry having a pH of about 6.5 to about 8.5 which is a mixture of water and about 20 to about 50 wt % sodium cyanurate. Also disclosed is a method of making a water-monosodium cyanurate hydrate gel-like slurry. A slurry is formed in water of about 20 to about 50 wt % cyanuric acid. Sodium hydroxide is added to the slurry in an amount of about 90 to about 100% of stoichiometric over a period of about 40 minutes. Water can be disinfected by adding to the water an amount of water-monosodium cyanuric hydrate gel-like slurry according to this invention equivalent to a concentration of cyanuric acid in the water of about 25 to about 150 ppm and an amount of a source of chlorine sufficient to maintain a concentration of chlorine in the water between about 0.1 and about 5.0 ppm.

13 Claims, 6 Drawing Sheets

MONOSODIUM CYANURIC ACID SLURRY

BACKGROUND OF THE INVENTION

This invention relates to a stable, gel-like slurry having a pH of about 6.5 to about 8.5 containing about 30 to about 40 wt % (dry basis) of a monosodium cyanurate monohydrate. It also relates to the preparation of that slurry and its use in swimming pools and other water systems.

Cyanuric acid (CYA) is used in swimming pool water at levels from 25 to 150 ppm (parts per million by weight) to stabilize hypochlorous acid from sunlight decomposition. CYA is added to swimming pool water upon start up of the pool with fresh water or on a routine basis by those customers who use forms of chlorine other than chlorinated isocyanurates to maintain desired CYA concentration.

CYA is typically in a dry (containing 6 wt % or less water), granulated form. Typical means of application are to broadcast over the pool or to slurry the granules in water and pour the slurry down the pool skimmer. CYA is very slow to dissolve and can take several days to dissolve if broadcast into a pool. Until the CYA has been dissolved for at least 24 hours the pool operator must be careful not to backwash the filter as this would flush the CYA granules out of the filter before they can dissolve in the pool water. The CYA is a weak acid (pH about 3.0) and usually the pool water pH must be adjusted after it has been added.

Slurries of pure CYA untreated with caustic tend to settle and form hard cakes that are typically difficult to resuspend, making them a poor choice as a commercial slurry product. A typical CYA slurry in a half gallon vessel takes several minutes of constant shaking to resuspend the solids. If settled with vibration (such as occurs in transportation) the solids are even more difficult to resuspend. In some cases, after prolonged storage, the cakes become hard and can be removed from the container only by breaking the container open and physically agitating the cake.

Attempts have been made to improve the performance of CYA by reducing its particle size or by adding a dispersant, such as surfactant, but were not successful. The addition of polymers to pure CYA results in a stable slurry, but the dispersant properties of the slurry are usually diminished and an additional chemical is introduced into the pool.

It is well known that monosodium cyanurate (MSCY) has some advantages over CYA because it is more soluble and has a more neutral pH. But the MSCY products proposed have all been dry formulations that are slower to dissolve than slurries and require more capital to manufacture. U.S. Pat. No. 4,233,444, for example, discloses making monoalkali metal cyanurate continuously in a two reactor system. This patent was mainly for the production of chlorinated isocyanurates, but it mentions that monoalkali cyanurates can be used for stabilizing chlorine-containing water if the metal cyanurates are recovered by centrifuging and drying. This technology, as well as other technology for producing dry MSCY, is not believed to be commercially practiced due to the large capital requirements required to make it, including two reactors, a centrifuge, dryer, and possibly other solids handling equipment, such as either a mill or a compactor and screening equipment.

SUMMARY OF THE INVENTION

We have discovered that MSCY monohydrate (MSCYH) can be produced in the form of a gel-like slurry that is stable and readily dissolves in water. The gel-like slurry of this invention is superior to conventional products for stabilizing chlorine in a swimming pool because, when poured into the pool, it easily disperses and dissolves within seconds, faster than either CYA or dry MSCY granules. Also, the product is close to neutral in pH, requiring less pH adjustment of the pool. The slurry of this invention remains in a pourable form over time and little or no shaking is required prior to its use.

The MSCYH slurry of this invention is thick and viscous, and exhibits pseudo-plastic properties that make it resistant to settling (dewatering); it is easily resuspended by shaking. Based on typical slurry behavior and prior work with CYA and alkali metal salts of CYA, these properties were not expected. The process for making the slurry requires only one mixing tank and therefore uses much less capital equipment than is required to produce conventional MSCY.

BRIEF DESCRIPTION OF THE DRAWINGS

FIG. 3 is a photomicrograph of the starting CYA slurry crystals used in the slurry preparations described in the examples. The microscope used was a Reichert. These CYA crystals were generated in an industrial process in which crude CYA (containing 20% ammelide & amelide impurities) from a kiln process is hydrolyzed utilizing sulfuric acid, followed by a filtration step and then reslurried in water. The slurry was placed on a glass slide with a cover slip and the photomicrograph was taken at 110× magnification.

DESCRIPTION OF THE PREFERRED EMBODIMENTS

Making the Gel-Like Slurry

The preferred process for making the gel-like slurry of this invention is to slowly mix sodium hydroxide (caustic) with an aqueous slurry of CYA. The sodium hydroxide is preferably in solution, but the solution should be at least 35 wt % sodium hydroxide as lower concentrations may not result in the unique gel-like slurry of this invention; the sodium hydroxide solution is preferably about 45 to about 55 wt % sodium hydroxide and 50 wt % sodium hydroxide is most preferred as it is readily available. Sodium hydroxide is required because the gel-like properties were not observed when other alkali metal hydroxides, such as potassium hydroxide or lithium hydroxide, were used.

The aqueous slurry of CYA should contain about 20 to about 50 wt % CYA as lower amounts result in a thin slurry and higher amounts result in a paste too thick to handle, slow the reaction time, and form smaller crystals with a lower length/diameter ratio. Preferably, the slurry of CYA contains about 25 to about 35 wt % CYA. Since the use of coarse CYA particles requires a longer reaction time, it is preferable to use CYA particles in the slurry that have a particle size of less than 300 µm.

The CYA and sodium hydroxide should be mixed in a mole ratio of sodium hydroxide to CYA of about 0.8 to about 1 (i.e., the sodium hydroxide is about 80 to about 100% of stoichiometric). Slightly higher mole ratios result in a higher pH, which would require a corrosive label on the product and would cause the slurry to rapidly lose its pseudo-plastic properties. It was also observed that the crystal habit of the slurry solids changed from micro fiber crystals to much larger irregular block crystals at mole ratios slightly over 1. Also, slurries with slightly higher mole ratios (1.0 to 1.5) have lower apparent viscosities and dewater on settling to a greater extent. At lower mole ratios, the slurries contain more unreacted particulate CYA, which can settle out of solution forming a cake that is more difficult to resuspend. The preferred mole ratio is about 0.95 to about 1.0 (i.e., about 95 to about 100% of stoichiometric). The sodium hydroxide is preferably added to the CYA slurry. Reversing the order of addition does not work well because, at the desired slurry concentration range, a thick paste is formed at a mole ratio of sodium to CYA near 2.0, which is very difficult to mix, stops the addition of CYA, and results in a mixture of various salts of CYA.

To obtain the unique gel-like slurry of this invention, the mixing should be done slowly over a period of at least 40 minutes and preferably over about 1 to about 4 hours. A long period of good mixing is required to react all the CYA with the sodium hydroxide and form the desired micro fiber-like crystals of MSCYH. Insufficient mixing time or too high a rate of caustic addition can result in the formation of grit or chunks in the slurry of other crystal forms of MSCY, other CYA salts, or unreacted CYA particles. These particles dissolve more slowly and can settle out, forming a hard cake.

Good mixing is important to insure that all of the caustic reacts with the CYA. Because the slurries of this invention are so viscous, special mixing equipment designed for viscous slurries should be used in the reaction vessel. Some examples of such equipment are helical coil agitators or agitators with multiple turbine impellers. Poor mixing can result in a slurry having poor gel properties and poor consistency, due to areas of unreacted CYA and the presence of crystals of higher salts of CYA.

In the preferred process, the rate of addition of caustic near the end of the caustic addition is controlled to keep the maximum slurry pH below about 8.5. This insures that caustic is being added no more rapidly than it can react with the solid CYA and that the final mole ratio is about 0.8 to about 1.0. When CYA solutions in water are reacted with sodium hydroxide they exhibit a sharp increase in pH near a pH of 8.95, the breakpoint for MSCYH. Near the end of the reaction, a sharp rise in slurry pH for the addition of a small amount of caustic is an indication that nearly all the CYA has reacted. The pH of the slurry then slowly drops as the remaining CYA reacts. Preferably, the sodium hydroxide addition should end when the pH of the slurry is stable and is between 7.0 and 8.0.

The caustic addition with good mixing is preferably done without heating or cooling the slurry. The reaction takes place at ambient (room) temperatures, but some temperature rise of the slurry (about 15° C.) occurs as the caustic reacts with the CYA. Higher or lower temperatures could be used if desired.

The Gel-Like Slurry

The resulting gel-like slurry has about 20 to about 40 wt % total solids (dry basis) and is preferably about 28 to about 35 wt % solids (dry basis). The solids are primarily MSCYH crystals, the reaction product of CYA and the sodium hydroxide. At room temperature, the solid content of the slurry is about 99 wt % as solids and about 1 wt % in saturated solution. Higher concentrations of MSCYH (i.e., above about 40 wt %, dry basis) have not been tested due to difficulties in handling the thick slurry. At concentrations of MSCYH under 20 wt %, the slurry settles to a stable solids slurry phase of about 30 wt % with a layer of water above it. This settled stable slurry is still pourable and is easily redispersed by shaking. To avoid needlessly packaging and shipping water, the water can be decanted off.

Figure 1:
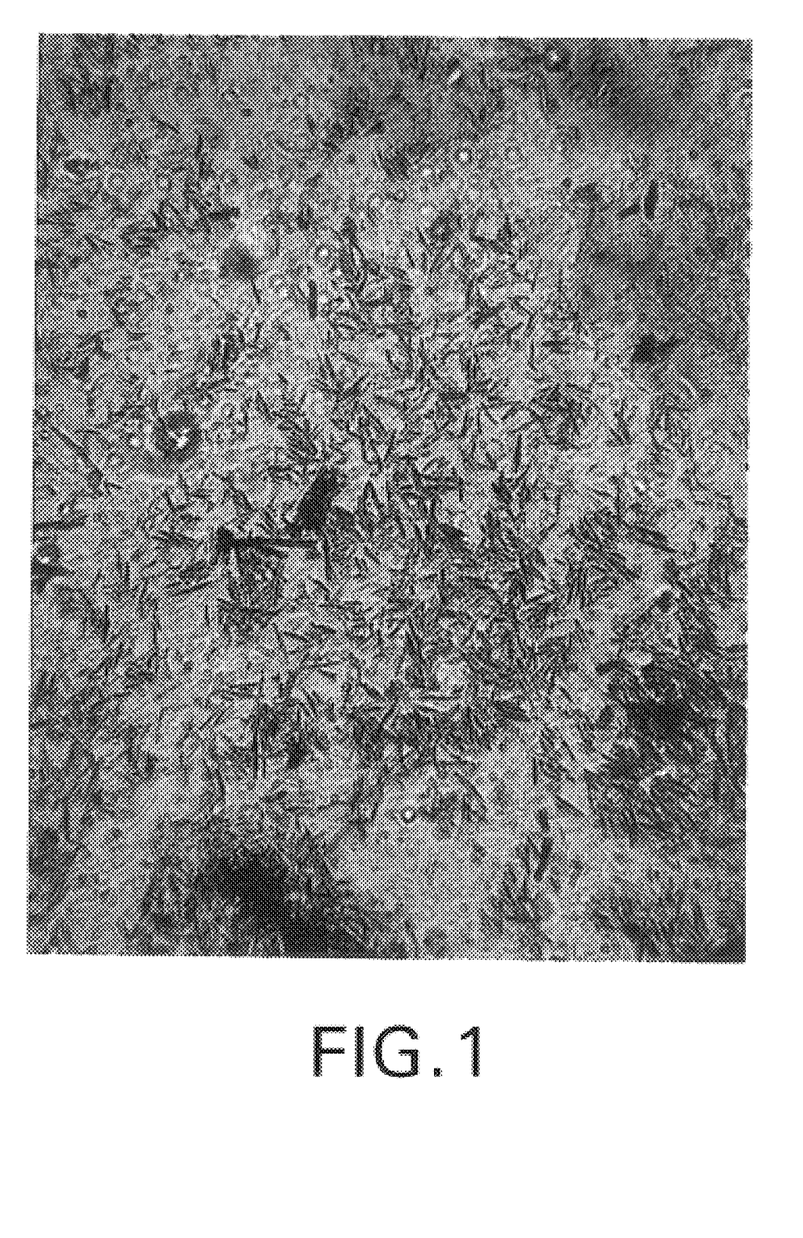
FIG. 1 is a photomicrograph of an MSCYH slurry according to this invention, prepared as described in Example 5. The microscope used was a Reichert. The slurry was placed on a glass slide with a cover slip and photo taken at 280× magnification.
Figure 2:
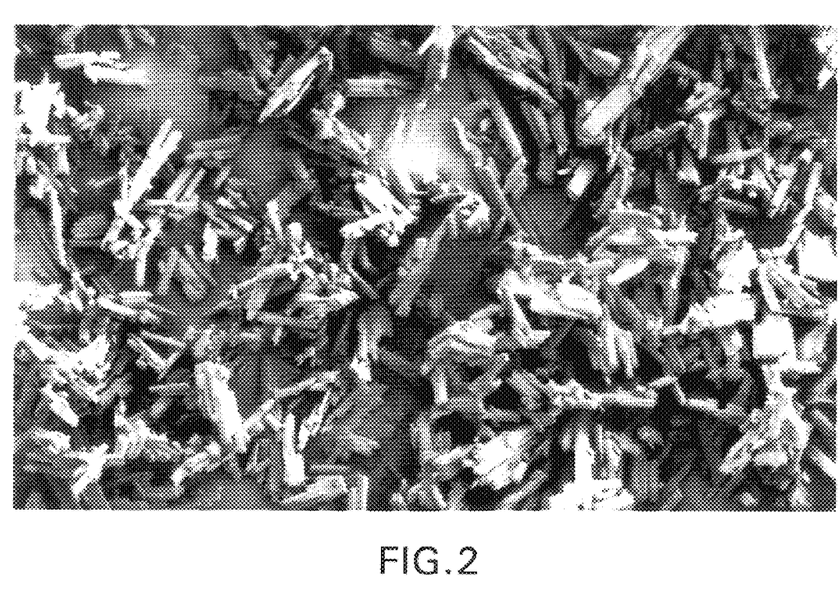
FIG. 2 is a scanning electron microscope (SEM) photograph of a dried sample of a MSCYH slurry prepared as described in Example 6. The dry crystals were mounted on large SEM sample stud and coated with silver to insure good conductivity. This photomicrograph was taken on a JEOL 5800LV SEM with a PGT/IMIX energy dispersive X-ray spectrometer at 1000× magnification.

The micro-fiber form of the MSCYH crystals may be responsible for the unique gel-like properties of the MSCYH slurry as well as very fast dissolution in pool water. The MSCYH crystals are needle-like crystals that look like finely milled asbestos (asbestiform crystals), many with a length to diameter ratio of 5 to 20. A typical crystal would have a diameter of 1 or 2 µm and be 10 to 20 µm long. The largest crystals have a diameter of up to 5 µm and are 40 to 70 µm long. The crystals surfaces are not well developed or organized, leaving a rough milled fibrous appearance (FIG. 1). The slurries have the appearance of a micro fiber slurry of finely milled asbestos or paper pulp (FIG. 2). It appears that the MSCYH crystals form a tangled mass that holds a significant quantity of free moisture, and that structure may be responsible for giving the settled cake pseudo-plastic flow properties that are similar to soft serve ice cream or catsup. The gel-like MSCYH slurry has a viscosity of about 50,000 to about 500,000 mPa·s and preferably the viscosity is about 50,000 to about 200,000 mPa·s.

Figure 3:
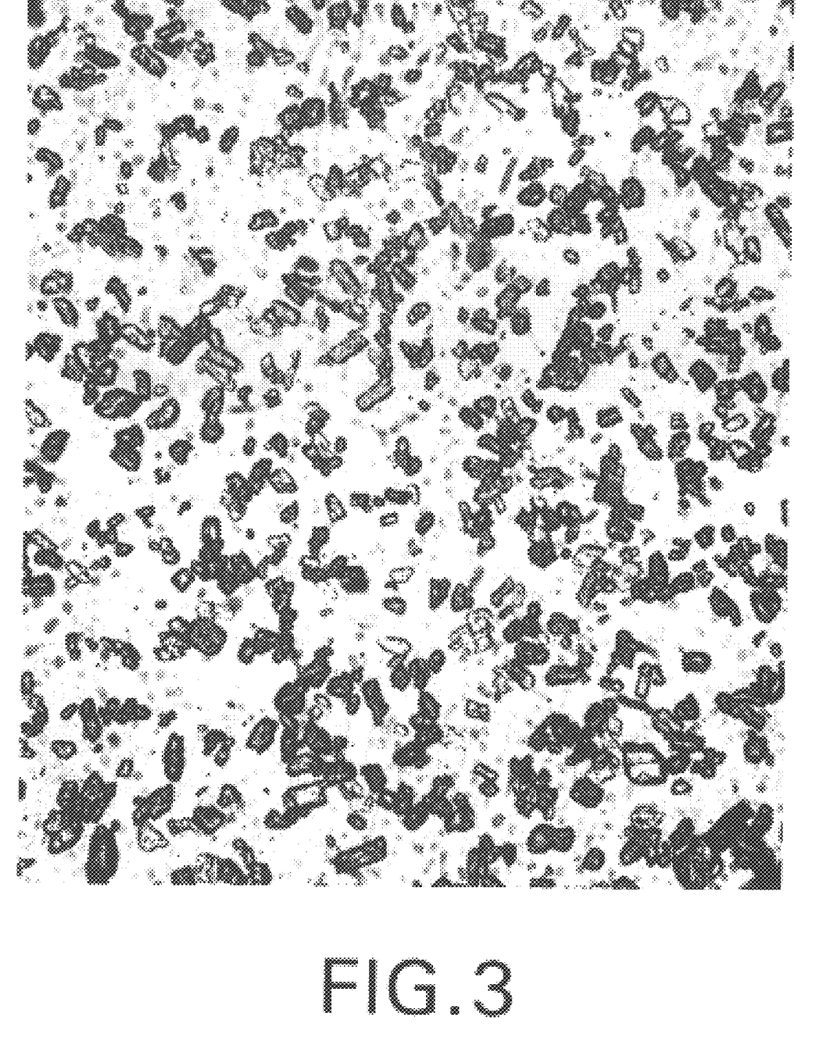
Figure 4:
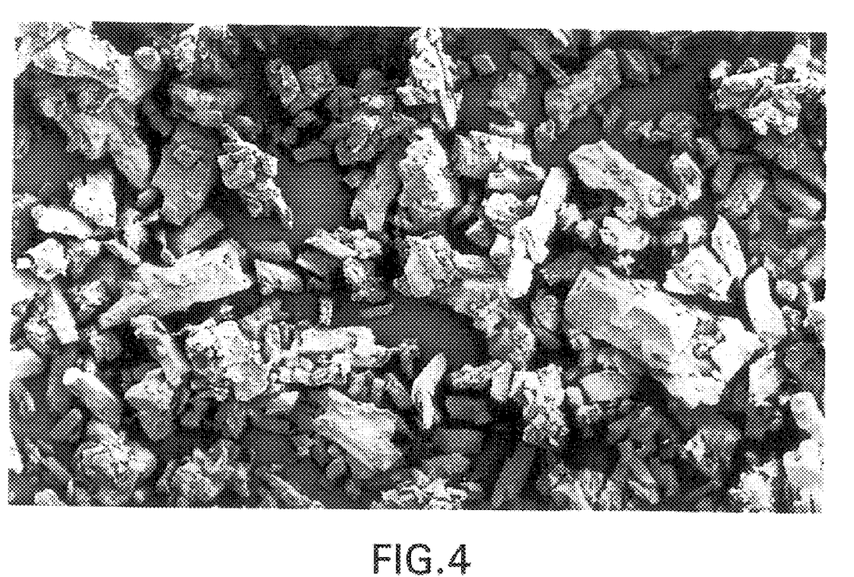
FIG. 4 is an SEM photomicrograph of a dried sample of the same slurry crystals shown in FIG. 3. The dried crystals were mounted on a large SEM sample stud and coated with silver to insure good conductivity. This photomicrograph was taken on a JEOL 5800LV SEM with a PGT/IMIX energy dispersive X-ray spectrometer at 110× magnification.

The starting CYA slurry crystals are irregularly blocked shaped crystals (see FIGS. 3 and 4) that rapidly settle out of a slurry. These crystals are much larger than the MSCYH crystals, with a maximum size near 200 µm long by 100 µm wide. The CYA crystals had many partially developed layers or facets on the surface of the crystals, giving a rough surface. The CYA crystals had apparent length to diameter ratios from 1 to 3 and a mean average size measured by a Lasentec Lab-Tec 1000 particle size analyzer of 56 µm (assuming spherical equivalent diameter).

Potassium cyanurate salt crystals (FIG. 5) are small irregular block crystals with no well-developed faces or sharp edges. Most edges are rounded and the crystals appear lumpy with an apparent length to diameter ratio less than 4. The largest crystals are about 6 µm in diameter and up to 25 µm in length at the maximum length to diameter ratio. Lithium cyanurate salt crystals (FIG. 6) are similar in appearance and size to the potassium salt crystals and more rounded. Slurries of these two salts were not resistant to settling as the MSCYH slurries were and they had different flow properties.

Because the MSCYH slurry of this invention is so viscous, it is preferable to add about 0.05 to about 4 wt % of a surfactant, phosphonate, or another viscosity reducer to lower its viscosity and aid in mixing and pumping. The slurry can be stabilized against settling by the addition of about 0.1 to about 1.0 wt % of a dispersant, such as a lignosulfonate, an alginate, or a polymer, such as xanthan gum, but under preferred conditions these agents are not necessary due to the natural pseudo-plastic properties of the slurry.

The gel-like slurry of this invention can be used to treat swimming pools, hot tubs and spas, cooling towers, artificial ponds, lagoons, cooling ponds, decorative fountains, and other bodies of water exposed to direct sunlight. A typical practice is to add an amount of a water-MSCYH gel-like slurry according to this invention sufficient to maintain a concentration of CYA in the water between about 25 and about 150 ppm and an amount of a source of chlorine sufficient to maintain a concentration of chlorine in the water between about 0.1 and about 5 ppm. Preferably, the concentration of CYA is about 25 to about 100 ppm and the concentration of chlorine is maintained at about 1.0 to about 4.0 ppm. Examples of sources of chlorine include calcium hypochlorite, sodium hypochlorite, lithium hypochlorite, chlorine gas, and chlorine liquid.

The following examples further illustrate this invention. The CYA used in the examples had a particle size distribution between 4 and 300 $\mu$m with a mean average size of 60 $\mu$m (spherical equivalent) as measured by a Lasentec Lab-Tec 1000 particle size instrument.

EXAMPLE 1

Preparation of MSCYH Slurry with a Viscosity Modifying Agent

A 2.5 liter reactor equipped with a Lightnin© model TSR1515 mixer having a 6.9 cm (2.7 inch) diameter A-100 impeller and a pH probe was charged with 1963 g of an aqueous slurry containing 33 wt % finely powdered CYA (80 wt % less than 200 mesh). Approximately 2 g of Monsanto's "Dequest 2010," a sequesterant, was added to the slurry. The slurry was agitated at 600 rpm with the agitator drawing about 1.33 W until it appeared to be well mixed. A 50 wt % caustic solution was added to the slurry at an initial rate of 3 g/min. The slurry pH increased from 1.6 to 7.4 after 10 minutes, when 36 additional grams of 50 wt % caustic were added. The slurry seemed less viscous and agitation was reduced to 530 rpm with good mixing; the agitator power draw fell to 0.3 W. The rate of addition of caustic was decreased to 2.0 g/min and it was observed that the pH began to gradually decrease. After 1 hour, 160 g of 50 wt % caustic had been added. The pH was 6.8 and the mixture appeared thicker and more viscous. At 1 hour and 10 minutes the agitator speed was increased to 600 rpm to maintain some mixing of the top surface of the slurry. The power draw was now 0.8 W, the pH was 6.7, and a total of 182 g of caustic had been added. The slurry rapidly got much stiffer, requiring increases in agitator speed and power for every 40 g of 50 wt % caustic added; the pH was observed to increase slightly. After 1 hour and 40 minutes, 337 g of 50 wt % caustic had been added and the agitator speed was 900 rpm and pulling 8.6 W. The slurry was at a pH of 6.8 and its temperature was 40° C. Caustic addition continued until after 3 hours when the pH was 7.9 and 431 g of 50 wt % caustic had been added. The mixing conditions were at 1015 rpm and the agitator was drawing 13.5 W. The slurry, which had a solids concentration of 35 wt %, was diluted with water to a concentration of 30 wt % solids. An X-ray diffraction pattern of an air dried sample of these slurry solids indicated the crystals were MSCYH.

Approximately 3 months after being made, a sample of the slurry was diluted and titrated with acid and then back titrated with caustic to determine the percentage of MSCY that was present. The slurry solids were found to be 98.8 wt % MSCY with the remainder CYA. The diluted (100 to 1) sample had a pH of 8.9, while the concentrated slurry pH was measured at 7.4. The slurry particle size was measured on a Lasentec Labtec 1000 device and found to have a mean particle size of 21 $\mu$m with a distribution standard deviation of 9.7 $\mu$m. The slurry had an apparent density of 1.16 g/cc.

EXAMPLE 2

Preparation of MSCYH Slurry Without a Viscosity Modifying Agent

A slurry of 30 wt % MSCY was prepared without the use of the Dequest sequesterant. The 2.5 liter reactor equipped as in Example 1 was charged with 1770 g of a 27.5 wt % CYA slurry made from powdered CYA (80 wt % −200 mesh). The slurry was agitated at 300 rpm and had an initial pH of 2.1 at a temperature of 20.6° C. A 50 wt % solution of NaOH was added at a rate of 2.7 g/min. After 20 minutes of addition (66.7 g NaOH, pH 7.37, 25.7° C.) the degree of mixing was not good and the agitation was increased to 370 rpm. Agitation was increased to 400 rpm at 40 minutes (110.9 g NaOH added, pH 7.22, temperature 28.9° C.). As the mixture thickened, the agitation was increased. Several times, when the pH rose above 8.0, the addition of caustic was stopped; it was restarted as the pH dropped back to under 7.0 due to the slow reaction of the caustic with the CYA. After 2.0 hours, the caustic addition was stopped. The final temperature of the slurry was 35.9° C., 272 g of caustic slurry had been added, and the agitator was at 611 rpm with a power input of 1.14 W into the slurry. The slurry pH was 8.08.

The slurry had a solids content of 29.5 wt % (unhydrated basis) and was observed to have a much higher viscosity than the slurry in Example 1. The slurry had an apparent density of 1.16 g/cc and a mean particle size of 28.2 $\mu$m, as measured on a Lasentec Labtec 1000 instrument, with a distribution standard deviation of 13.4 $\mu$m. Approximately 3 months after being made, the slurry had a pH of 7.26, which increased to 8.11 when diluted 100 to 1. A sample of the slurry was diluted with water and titrated with acid and then base to determine the amount of MSCY present. It was found to be 93 wt %, with the remainder being CYA. This slurry had an apparent density of 1.16 g/cc.

EXAMPLE 3

Comparison of Flow Properties of MSCYH Slurries with CYA Slurries

A slurry of 30 wt % CYA was prepared from the same CYA wet cake used to make the above two samples. The slurry had an apparent density of 1.198 g/cc. The CYA slurry particle size distribution was measured on a Labtec 1000 instrument and was found to be 49.4 $\mu$m with a distribution standard deviation of 30.9 $\mu$m.

The viscosity of the three slurry samples was first measured on a Nametre vibrating sphere viscometer at 25° C. The CYA slurry could be stirred well enough with a magnetic stir-bar and gave a viscosity of 1.8 mPa·s. The two MSCYH slurries prepared above could not be stirred well enough to use this device.

Viscosity measurements of the MSCYH slurries (Examples 1 and 2) were made at 25° C. using with a Brookfield helipath stand, where a T-Bar and a wire spindle were used in a constantly rising and lowering motion to prevent channeling. For the slurry in Example 1, which contained some Dequest 2010 sequesterant, a very high viscosity was observed to decrease from 126,360 mPa·s at a spindle speed of 0.6 rpm to 94,224 mPa·s at 1.5 rpm spindle speed. The sample from Example 2, which did not contain Dequest 2010 sequesterant, had an even higher viscosity of 433,680 mPa·s at a spindle speed of 0.6 rpm. Again, when the spindle speed was increased to 1.5 rpm the apparent viscosity decreased to 343,200 mPa·s. Because the viscosity was observed to decrease with increasing shear rates, these two slurries exhibited pseudo-plastic properties. More extensive tests were not conducted to determine whether the slurries were thixotropic (i.e., viscosity changes with time and shear history).

Both MSCYH slurries had a high yield value (i.e., did not flow), based on observations that the material formed a peak when poured, as does catsup or soft serve ice cream; the slurry then flows out when vibrated or tapped. The very high viscosity at rest is effective in stabilizing the suspension from settling. When shear is applied (as in pouring, mixing, or pumping), viscosity is reduced as the shear rate increases. The solutions can then be poured or mixed readily and pumping energy is reduced.

EXAMPLE 4

Comparative Settling Experiments of MSCYH Slurries and CYA Slurries

A 100 ml portion of each of the three slurries (the MSCYH slurries of Examples 1 and 2 and the CYA slurry of Example 3) were poured into separate 100 ml graduated cylinders and allowed to settle for 5 days. only a 1 vol % layer of clear solution formed on top of the solid slurry phase for samples from Examples 1 and 2 after 5 days, which meant that the slurry still occupied 99 vol % of its original volume. The 30 wt % slurry of CYA from Example 3 (60 μm mean particle size) settled to 6 vol % clear solution phase after 9 minutes and this phase increased to 11 vol % after 5 days in the same experiment. All three graduated cylinders containing the slurries were then vibrated for one hour on a Gilson laboratory vibrator. In both the MSCYH samples the solid phase settled slightly to 98 vol % of its original volume. The solid phase in the CYA sample listed above settled to 72 vol % of its original volume.

The two MSCYH samples (from Examples 1 and 2) were emptied from the graduated cylinders by pouring and tapping much like a catsup bottle. From the Dequest 2010© (Example 1) sample, 96 vol % of the MSCYH was removed by pouring and gently shaking, leaving a thin film coating the inside of the cylinder. From the MSCYH sample (from Example 2) 92 vol % of the slurry was removed with more vigorous tapping. Only 36 vol % of the CYA slurry could be removed from the cylinder even with the most vigorous shaking.

EXAMPLE 5

Preparation of the MSCYH Slurry Used in FIG. 1

An MSCYH slurry was prepared in the 2.5 liter reactor described in Example 1. The reactor was filled with 2,084 g of an aqueous slurry containing 25 wt % finely powdered CYA (80 wt % less than 200 mesh). Agitation was started at 241 rpm and the slurry had an initial pH of 2.4. A 50 wt % sodium hydroxide solution was added to the slurry at 15 g/min. After 8 minutes the slurry appeared thick and agitation was increased to 460 rpm. The slurry had a pH of 7.2 and 122 g of caustic had been added. The slurry appeared to become thicker and the agitation speed was increased. After 20 min, 275 g of caustic had been added. The agitator was at 700 rpm, the slurry pH was 6.9 and the slurry was at 42° C. After 40 min, 339 g of caustic had been added. The slurry suddenly became less viscous as the pH peaked at 8.1. The agitator speed had been increased to 797 rpm to maintain mixing and the slurry temperature was 43° C. The rate of caustic addition was slowed, the pH dropped back to 6.7, and the slurry became more viscous. Caustic was added slowly a few grams at a time to keep the pH between 7.0 and 8.0. After 83 min, caustic addition was stopped; 360 g of caustic had been added. The pH was 7.3 and an agitator speed of 860 rpm was required to see the slurry flowing at the surface. The slurry was allowed to mix an additional 16 min and the pH was observed to drop to 7.02. A sample of the slurry was dried and it was found to contain 30 wt % (unhydrated solids).

EXAMPLE 6

Preparation of the MSCYH Slurry Used in FIG. 2

This 32 wt % solids (unhydrated basis) MSCYH slurry had a mole ratio of 0.8 sodium hydroxide to CYA. The slurry was prepared in a smaller laboratory reactor with an oversized agitator. First, 320 g of an aqueous slurry containing 47 wt % fine powder (80 wt % less than 200 mesh) CYA was charged to the reactor and agitated. Then 180 g of water was added to the slurry with mixing. Next, 74.4 g of 50 wt % caustic was added over a period of 90 min. The resulting slurry was thick and creamy. After two additional hours of stirring, the slurry had a pH of 7.3.

EXAMPLE 7

Figure 5:
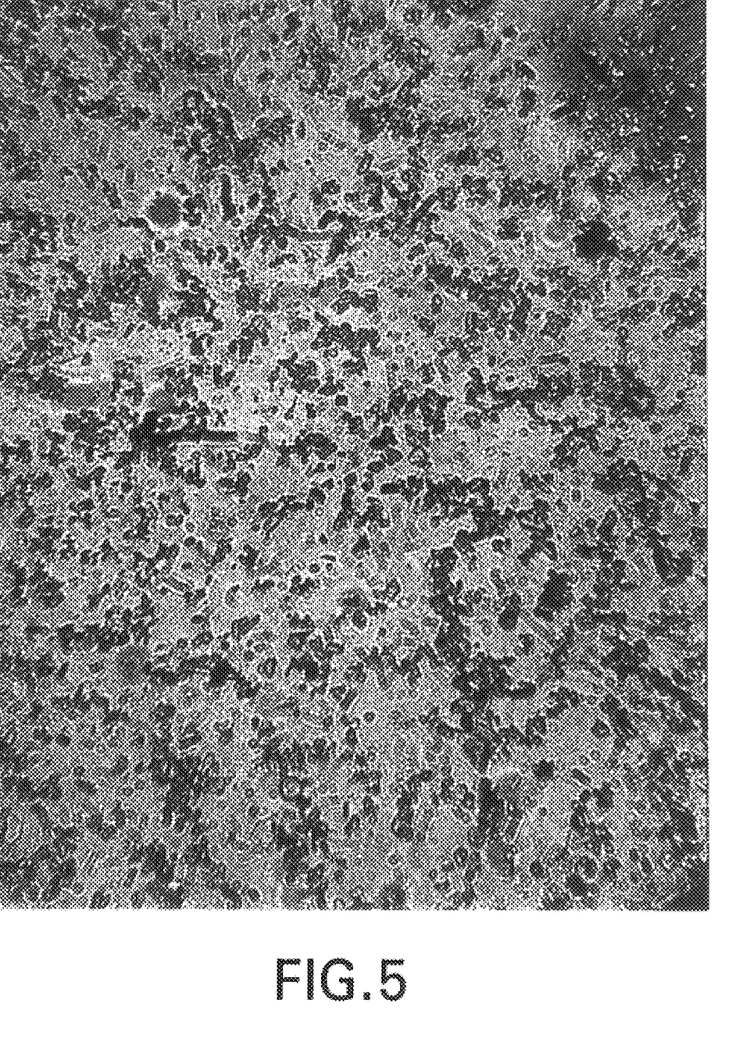
FIG. 5 is a photomicrograph of potassium cyanurate crystals from a 30.9 wt % slurry prepared as described in Example 7. The slurry was placed on a glass slide with a cover slip and the photo was taken at 280× magnification.

Preparation of the Potassium CYA Slurry Used in FIG. 5 for Comparison with MSCYH Slurries This 30.9 wt % potassium cyanurate slurry had a mole ratio of 1:1 based on weights and composition of the ingredients used. The sample was prepared in the same laboratory reactor used in Example 6. First, 320 g of an aqueous slurry containing 47 wt % fine powder (80 wt % less than 200 mesh) CYA was charged to the reactor and agitated. Then 180 g of water was added to the slurry with mixing. Next, 130.4 g of 50 wt % KOH was added slowly to the slurry over two hours with continuous mixing. The slurry had a pH of 6.94. The slurry viscosity never got as high as the MSCY slurries of the same concentration and did not have the gel-like properties of MSCY. The slurry was stirred an additional 4.5 hours and the pH was observed to increase to 7.4. After 24 hours, the slurry pH was 7.53. After 2 hours without agitation this slurry settled to a solids phase that was 93 vol % of the original slurry volume, with a clear liquid phase containing some dissolved solids above the solids phase. This sample had much greater settling than did the MSCYH slurries.

EXAMPLE 8

Figure 6:
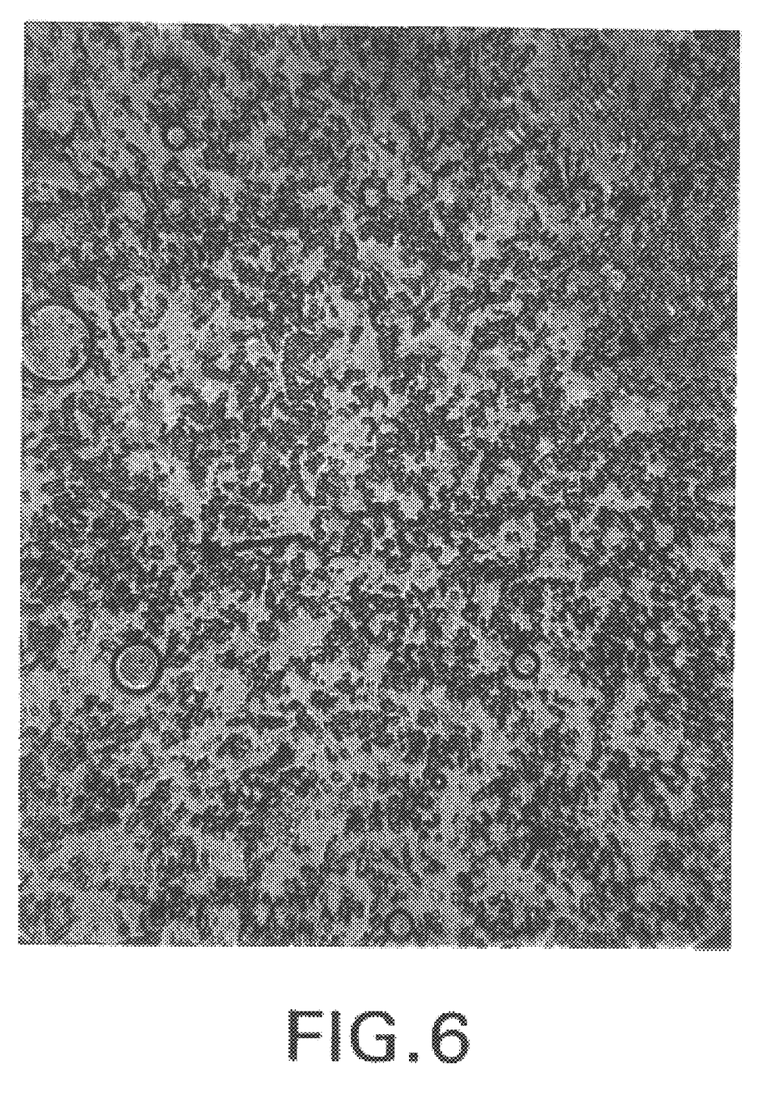
FIG. 6 is a photomicrograph of 30 wt % lithium cyanurate crystals prepared as described in Example 8. The slurry was placed on a glass slide with a cover slip and the photo was taken at 280× magnification.

Preparation of the Lithium CYA Slurry Used in FIG. 6 for Comparison with MSCYH Slurries This 37 wt % lithium cyanurate slurry had a mole ratio of 1:1 based on weights and composition of the ingredients used. The sample was prepared in the same laboratory reactor used in Example 6. First, 320 g of an aqueous slurry containing 47 wt % fine powder (80 wt % less than 200 mesh) was charged to the reactor and agitated. Next, 47.3 g of $LiOH.H_2O$ was slowly added with stirring over 80 minutes. The slurry had a pH of 7.66. After stirring for two more hours, the slurry pH was 6.52. This slurry was not as viscous as the MSCYH slurries and did not exhibit gel-like properties. With the agitator off, this slurry settled in 3 hours to a solids phase that was 81 vol % of the stirred slurry volume, with a clear liquid phase containing some dissolved solids above the solids phase.

What is claimed is:

1. A stable gel-like slurry having pseudo-plastic properties, a high yield value, and a viscosity of 50,000 to about 500,000 mPa·s comprising a mixture of water containing about 20 to about 40 wt %, calculated as unhydrated, of monosodium cyanurate monohydrate, said mixture having a pH of about 6.5 to less than 8.5.

2. A slurry according to claim 1 wherein said monosodium cyanurate monohydrate is about 99 wt % as solids and about 1 wt % in saturated solution.

3. A slurry according to claim 1 wherein the pH is 7.0 to 8.0.

4. A slurry according to claim 1 which includes about 0.05 to about 4 wt % of a viscosity reducer.

5. A slurry according to claim 1 which contains about 28 to about 35 wt % calculated as unhydrated monosodium cyanurate monohydrate.

6. A slurry according to claim 1 in which said monosodium cyanurate monohydrate is primarily in the form of asbestiform crystals having a diameter of about 1 to about 5 μm and a length of about 10 to about 70 μm and a length to diameter ratio of about 5 to about 20.

7. A water-monosodium cyanurate monohydrate stable gel-like slurry having pseudo-plastic properties, a viscosity of about 50,000 to about 500,000 mPa·s and a pH of about 6.5 to less than 8.5, made by mixing for at least 40 minutes about 20 to about 50 wt % cyanuric acid in water to which has been added at least a 35 wt % aqueous solution of sodium hydroxide in an amount that is about 80 to 100 wt % of stoichiometric.

8. A slurry according to claim 7 wherein said sodium hydroxide solution is about 45 to about 55 wt %.

9. A slurry according to claim 7 wherein the wt % of cyanuric acid in water is about 25 to about 30 wt %.

10. A slurry according to claim 7 wherein the amount of sodium hydroxide is about 95 to about 100 wt % of stoichiometric.

11. A slurry according to claim 7 wherein s aid mixing is for about 1 to about 4 hours.

12. A slurry according to claim 11 wherein the rate of addition of said sodium hydroxide solution is controlled to keep the maximum pH of said gel-like slurry below about 8.5.

13. A water-monosodium cyanurate monohydrate stable gel-like slurry having a viscosity of about 50,000 to about 500,000 mPa·s and a pH of about 6.5 to less than 8.5, made by mixing for about 1 to about 4 hours about 25 to about 30 wt % cyanuric acid in water to which has been added about 95 to 100 wt % of stoichiometric of a 45 to 55 wt % aqueous solution of sodium hydroxide, where the rate of addition of said sodium hydroxide solution to said cyanuric acid is controlled to keep the maximum pH of said gel-like slurry below 8.5.

* * * * *